US010401342B2

(12) United States Patent
Akiyama et al.

(10) Patent No.: US 10,401,342 B2
(45) Date of Patent: *Sep. 3, 2019

(54) EVOLVED GAS ANALYZER AND METHOD FOR ANALYZING EVOLVED GAS

(71) Applicant: HITACHI HIGH-TECH SCIENCE CORPORATION, Tokyo (JP)

(72) Inventors: Hideyuki Akiyama, Tokyo (JP); Kentaro Yamada, Tokyo (JP); Toshitada Takeuchi, Tokyo (JP)

(73) Assignee: HITACHI HIGH-TECH SCIENCE CORPORATION, Tokyo (JP)

( * ) Notice: Subject to any disclaimer, the term of this patent is extended or adjusted under 35 U.S.C. 154(b) by 279 days.

This patent is subject to a terminal disclaimer.

(21) Appl. No.: 15/356,579

(22) Filed: Nov. 19, 2016

(65) Prior Publication Data

US 2017/0146503 A1    May 25, 2017

(30) Foreign Application Priority Data

Nov. 20, 2015  (JP) ................................ 2015-227370
Sep. 6, 2016   (JP) ................................ 2016-173395

(51) Int. Cl.
*G01N 35/00*    (2006.01)
*G01N 33/00*    (2006.01)

(52) U.S. Cl.
CPC ... *G01N 33/0016* (2013.01); *G01N 35/00584* (2013.01); *G01N 2035/00346* (2013.01); *G01N 2035/00445* (2013.01)

(58) Field of Classification Search
CPC ......... G01N 33/0016; G01N 35/00584; G01N 2035/00445; G01N 2035/00346; G01N 21/72; G01N 21/71
See application file for complete search history.

(56) References Cited

U.S. PATENT DOCUMENTS 5,367,163 A * 11/1994 Otsuka .................. H01J 49/105
                                                     250/281
2008/0038163 A1* 2/2008 Boege ....................... B01L 7/52
                                                     422/600

(Continued)

FOREIGN PATENT DOCUMENTS

JP       11-118778 A      4/1999
JP       2002-372483 A    12/2002

*Primary Examiner* — Eric S. McCall
*Assistant Examiner* — Timothy P Graves
(74) *Attorney, Agent, or Firm* — Maschoff Brennan

(57) ABSTRACT

Disclosed herein are an evolved gas analyzer and a method for analyzing evolved gas, the apparatus cooling a sample holder in a short time without using excessive cooling performance and without providing the entire apparatus in an excessively large size, thereby enhancing analysis work efficiency. The apparatus 200 includes: a sample holder 20 holding a sample S; a heating unit 10 receiving the sample holder therein, and evolving a gas component G by heating the sample; a detecting means 110 detecting the gas component; a sample holder supporting unit 204L movably supporting the sample holder to move the sample holder to predetermined outer and inner positions of the heating unit; and a cooling unit 30 provided at an outside of the heating unit, and cooling the sample holder by being in direct or indirect contact with the sample holder, when the sample holder is moved to a discharging position.

7 Claims, 11 Drawing Sheets

(56) References Cited

U.S. PATENT DOCUMENTS

2011/0239792 A1* 10/2011 Sato ................. G01N 1/2226
　　　　　　　　　　　　　　　　　　　　　73/863.11
2014/0057770 A1* 2/2014 Holmes ............. B04B 5/0421
　　　　　　　　　　　　　　　　　　　　　494/10

* cited by examiner

EVOLVED GAS ANALYZER AND METHOD FOR ANALYZING EVOLVED GAS

CROSS REFERENCE TO RELATED APPLICATION(S)

This application claims the benefit of Japanese Patent Application No. 2015-227370, filed Nov. 20, 2015, and Japanese Patent Application No. 2016-173395, filed Sep. 6, 2016, which are hereby incorporated by reference in their entirety into this application.

BACKGROUND OF THE INVENTION

1. Technical Field

The present invention relates generally to an evolved gas analyzer and a method for analyzing evolved gas, the method analyzing gas components evolved by heating a sample, thereby identifying, quantifying, etc. the sample.

2. Description of the Related Art

In order to increase flexibility of resins, plasticizers such as phtalates, etc. are added to the resins. After 2019, four substances of the phtalates will be restricted under the restriction of hazardous substances directive (RoHS). Therefore, it is required to identify and quantify the phtalates in the resins.

The phtalates are volatile substances such that a conventional evolved gas analysis (EGA) is applied to analyze the phtalates. The EGA is a method used to analyze gas components evolved by heating a sample by using a gas chromatograph or using various analyzers applying mass spectrometry, etc.

In an evolved gas analysis, a sample is placed on a sample stage, and the sample is heated by the sample stage in a heating furnace. Alternatively, the sample is set on a holding tool, and the holding tool is inserted into the heating furnace to evolve a gas component for the analysis. In addition, after the analysis, the sample stage is naturally cooled to a room temperature, and the sample is changed and is heated from about the room temperature to start a next analysis. However, standby time to cool the sample stage is long, and thus, work efficiency of the entire analysis process is reduced.

Therefore, technology of cooling air in the heating furnace by flowing refrigerant gas through a duct positioned in the heating furnace is disclosed in Patent Document 1. Technology of bring a cooling device into contact with a sample stage in a vacuum chamber, which is a heating furnace, is disclosed in Patent Document 2.

DOCUMENTS OF RELATED ART (Patent Document 1) Japanese Patent Application Publication No. Hei. 11-118778
(Patent Document 2) Japanese Patent Application Publication No. 2002-372483

SUMMARY OF THE INVENTION

In Patent Document 1, excessive cooling performance is required to cool a heating furnace itself. A cooling device and the entire analysis apparatus are provided in a large size. Furthermore, extra energy and time is required to heat the heating furnace again.

In addition, in Patent Document 2, it is required to introduce a refrigerant, etc. from a cooling device in a vacuum chamber, which is a heating furnace, and thus configuration of an apparatus is complicated, and is provided in a large size.

Accordingly, the present invention has been made keeping in mind the above problems occurring in the related art, and an object of the present invention is to provide an evolved gas analyzer and a method for analyzing evolved gas, the apparatus cooling a sample holder in a short time without using excessive cooling performance and without providing the entire apparatus in an excessively large size, thereby enhancing analysis work efficiency.

In order to accomplish the above object, the present invention provides an evolved gas analyzer including: a sample holder holding a sample; a heating unit receiving the sample holder therein, and evolving a gas component by heating the sample; a detecting means detecting the gas component evolved by the heating unit; a sample holder supporting unit movably supporting the sample holder so as to move the sample holder to predetermined outer and inner positions of the heating unit; and a cooling unit provided at an outside of the heating unit, and cooling the sample holder by being in direct or indirect contact with the sample holder, when the sample holder is moved to a discharging position at which the sample is supplied on or removed from the sample holder.

According to the evolved gas analyzer, the sample holder is in contact with the cooling unit to cool the sample holder. Therefore, in comparison with natural cooling, the sample holder is rapidly cooled, and thus, analysis work efficiency is enhanced. In addition, for example, it is possible to measure a plurality of samples for quality management, etc. Furthermore, the sample holder is cooled at an outside of the heating unit such that the cooling unit is not exposed to high temperature air of the heating unit. Therefore, excessive cooling performance is unnecessary, and the cooling unit or the entire apparatus may be provided in a small size. In addition, air temperature in the heating unit is not reduced by cooling such that extra energy and time is unnecessary to heat the heating unit again.

In addition, it is unnecessary to provide the cooling unit in the heating unit, whereby the heating unit or the entire apparatus may be provided in a small size.

The cooling unit may include a cooling block being in contact with the sample holder.

According to the evolved gas analyzer, heat of the sample holder is cooled by the cooling block, thereby efficiently cooling the sample holder.

The cooling block may include: a contact portion being in contact with the sample holder at the discharging position; and a protruding portion extending toward the heating unit to surround the sample holder, a distance between the protruding portion and the heating unit being shorter than a distance between the contact portion and the heating unit.

According to the evolved gas analyzer, the sample holder is moved to the contact portion, which is depressed more than the protruding portion, and the sample holder is sufficiently moved to an outside of the heating unit. Therefore, capacity (heat capacity) of the cooling block increases by comparison with a cooling block having no protruding portion, thereby enhancing cooling performance.

In addition, in order to maintain the same capacity of the cooling block without the protruding portion, it is required to move the cooling block more toward the outside of the heating unit, whereby it results in a large size of the entire apparatus. Therefore, with the protruding portion, the entire apparatus may be provided in a small size.

The cooling unit may include an air cooling fan or air cooling fins cooling the cooling block.

According to the evolved gas analyzer, the structure of the cooling unit is simple, and thus, the entire apparatus may be provided in a small size or may have reduced costs, in comparison with the case when water cooling is applied to the cooling unit or with the case when a duct, which refrigerant gas flows through, is attached to the cooling unit.

The cooling unit may include an air cooling fan, air cooling fins, and a fan duct cooling the cooling block, wherein the air cooling fan is connected to a lower surface and a side surface of the cooling block, the air cooling fan is provided at a lower surface of the air cooling fan connected to the lower surface of the cooling block, and the fan duct extends from the air cooling fan toward an outside of the air cooling fan connected to the side surface of the cooling block, and functions as an air guiding plate guiding cooling air from the air cooling fan to the air cooling fins.

According to the evolved gas analyzer, the cooling block is cooled by the air cooling fins connected to the lower surface and to the side surface of the cooling block. In addition, the fan duct functions as the air guiding plate guiding the cooling air from the air cooling fan to the air cooling fins, whereby the cooling block is efficiently cooled.

A ratio C1/C2 of a heat capacity C1 of the cooling block to a heat capacity C2 of the sample holder may be within a range of 5 to 20.

According to the evolved gas analyzer, it is possible to provide the entire apparatus in a small size and to enhance the cooling performance.

The heating unit may include a heating unit heater heating an inside of the heating unit to a predetermined temperature, and the sample holder comprises a sample heater heating the sample.

According to the evolved gas analyzer, the heating unit heater heats (retains the heat of) air in the heating unit to the predetermined temperature, whereby temperature of the sample in the heating unit is prevented from being changed. In addition, the sample heater provided around the sample may locally heat the sample, and thus, the temperature of the sample rapidly increases.

The evolved gas analyzer may further include: an autosampler automatically supplying the sample on or removing the sample from the sample holder at an outside; and a sample holder moving unit moving the sample holder in cooperation with the autosampler, wherein the sample holder moving unit may include: a first spring part elastically biasing the sample holder in a direction towards to the cooling unit, when the sample holder is close to the discharging position; and a second spring part elastically biasing the sample holder in a direction towards to the heating unit, when the sample holder is moved into the heating unit, and is close to a measuring position at which the gas component is measured.

According to the evolved gas analyzer, when the sample holder is in contact with the cooling unit, the first spring part is compressed, and the first spring part elastically pressures the sample holder in a direction towards the cooling unit by using repulsive power. In case when the first spring part is not used, it is required to precisely match a last position of the sample holder with a contact position of the sample holder and the cooling unit, when the sample holder is close to the discharging position and the sample holder is in contact with the cooling unit. Therefore, it may be not easy to provide the sample holder and the cooling unit close to each other.

Therefore, the first spring part is provided, and the last position is set closer to the cooling unit over the contact position of the sample holder and the cooling unit, whereby the sample holder is in contact with the cooling unit.

In the same manner as the first spring part, the second spring part is compressed when the sample holder is in contact with the heating unit. The second spring part elastically pressures the sample holder in a direction towards the heating unit by using repulsive power. Therefore, last position of the sample holder is set closer to the heating unit over a contact position of the sample holder and the heating unit, whereby the sample holder is provided at the measuring position.

In addition, the sample may be automatically supplied on or removed from the sample holder by an autosampler at an outside.

An inner wall of the heating unit may be depressed toward an outside at a position around the sample in the sample holder, thereby forming a recess, wherein the recess may have a first recess portion and a second recess portion integrally, the first recess portion is located upstream in a flow direction of the gas component in the heating unit, the second recess portion is located downstream of the first recess portion in the flow direction, and meets the inner wall of the heating unit, and when viewed from a cross section of the heating unit along the flow direction, an outline of the second recess portion is located upstream of a normal of the inner wall relative to a contact point between the second recess portion and the inner wall in the flow direction.

According to the evolved gas analyzer, since the outline (line) of the second recess portion is oblique downstream in the flow direction, the gas component easily flows along the second recess portion downstream in the flow direction (namely, toward the detecting means). In addition, the outline (line) of the second recess portion may be a straight or curved line.

According to another aspect, there is provided a method for analyzing evolved gas, the method including: movably supporting a sample holder holding a sample so as to move the sample holder to predetermined outer and inner positions of a heating unit; receiving the sample holder in the heating unit to heat the sample; detecting a gas component evolved by the heating unit; and cooling the sample holder by bringing the sample holder into contact with a cooling block of a cooling unit provided at an outside of the heating unit, when the sample holder is moved to a discharging position at which the sample is supplied on or removed from the sample holder.

According to the described above, the evolved gas analyzer can cool the sample holder in a short time without using excessive cooling performance and without providing the entire apparatus in an excessively large size, thereby enhancing analysis work efficiency.

BRIEF DESCRIPTION OF THE DRAWINGS

The above and other objects, features and advantages of the present invention will be more clearly understood from the following detailed description taken in conjunction with the accompanying drawings, in which.

DESCRIPTION OF THE PREFERRED EMBODIMENTS

Figure 1:
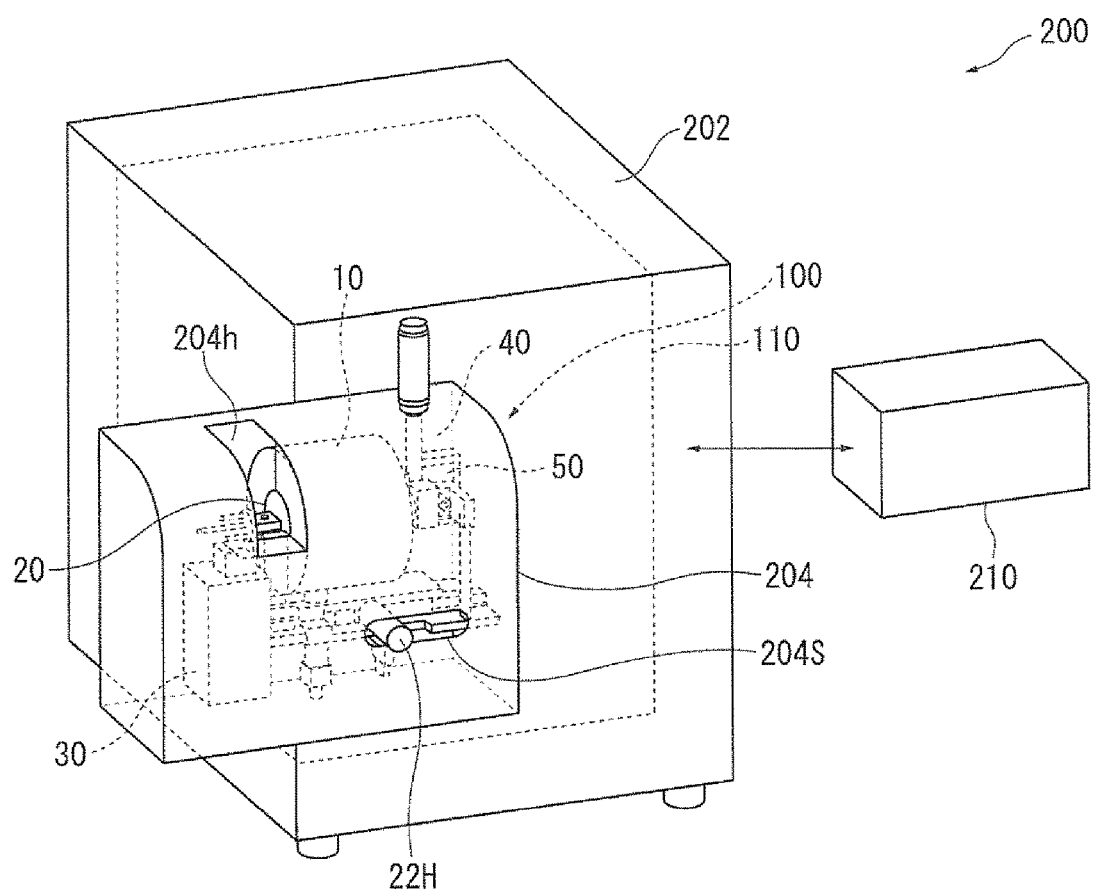
FIG. 1 is a perspective view showing the configuration of an evolved gas analyzer according to an exemplary embodiment of the present invention.
Figure 2:
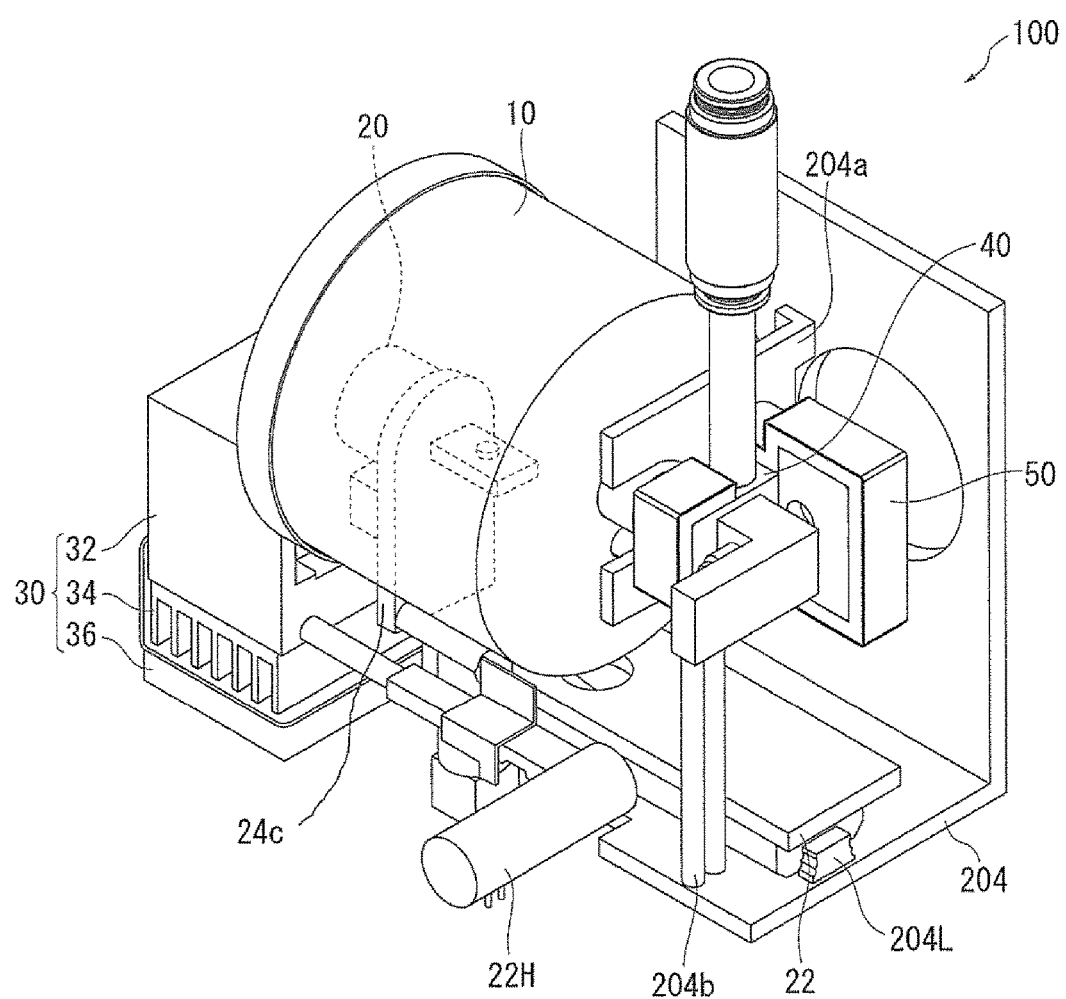
FIG. 2 is a perspective view showing the configuration of a gas evolving unit.
Figure 3:
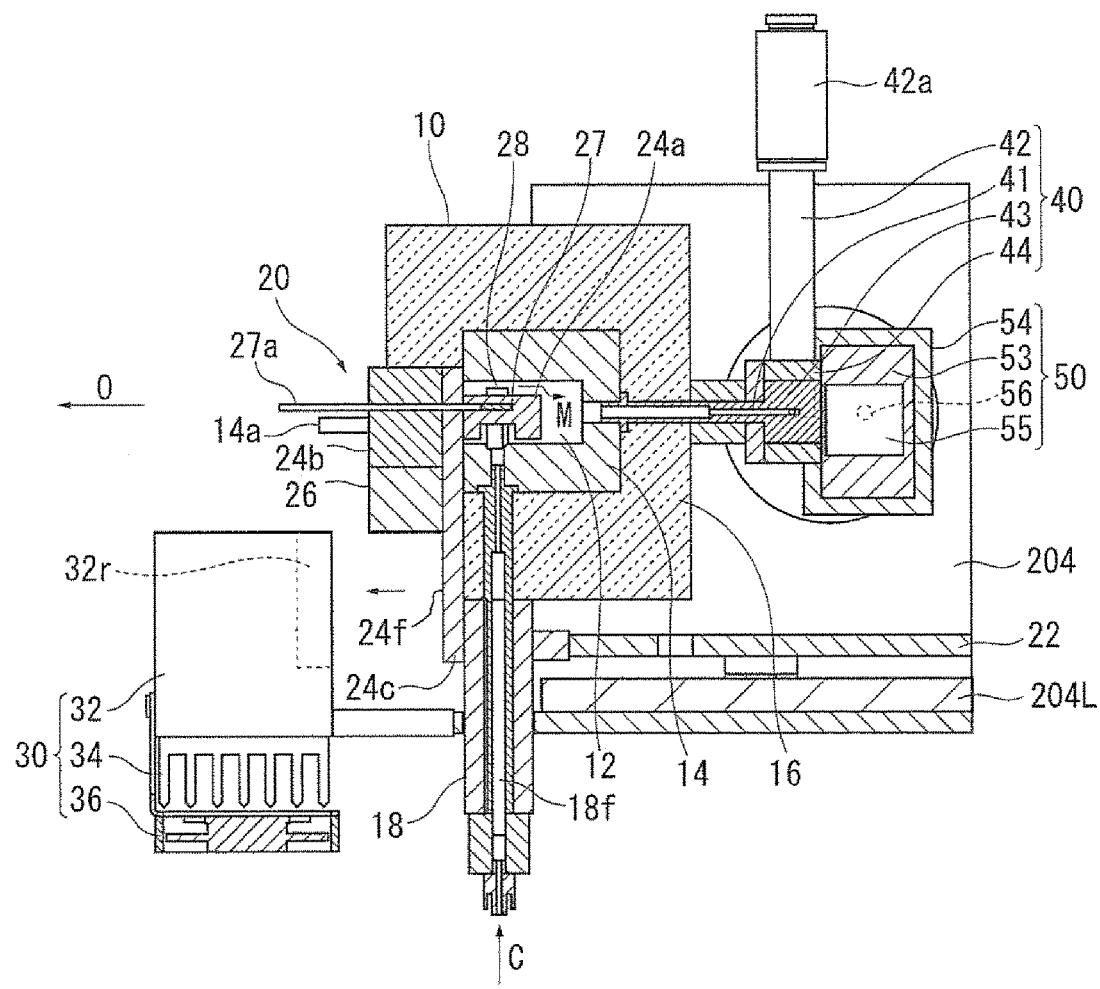
FIG. 3 is a longitudinal sectional view showing the configuration of the gas evolving unit.
Figure 4:
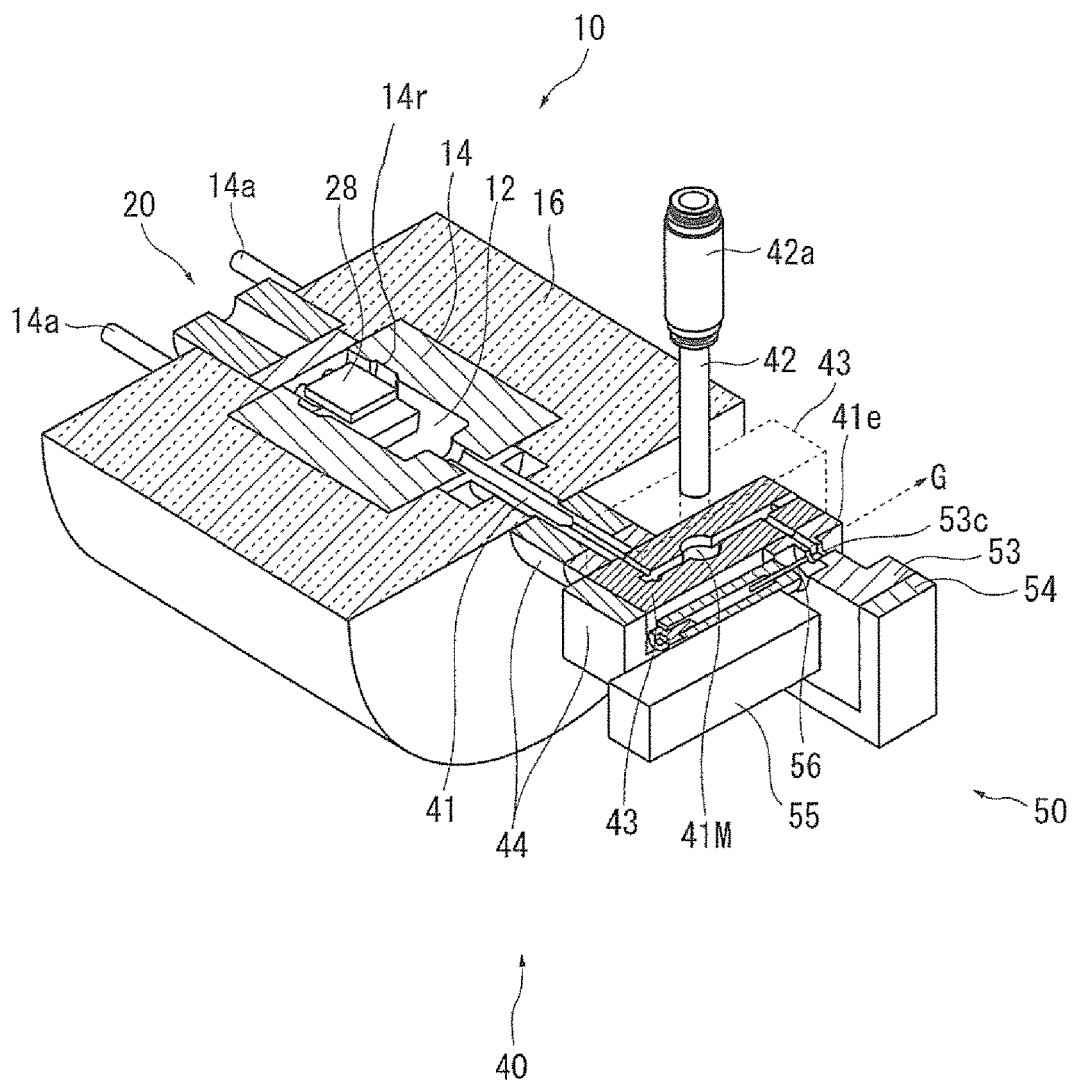
FIG. 4 is a cross-sectional view showing the configuration of the gas evolving unit.

Hereinafter, the exemplary embodiment of the present invention will be described with reference to the accompanying drawings. FIG. 1 is a perspective view showing the configuration of an evolved gas analyzer 200. FIG. 2 is a perspective view showing the configuration of a gas evolving unit 100. FIG. 3 is a longitudinal sectional view showing the configuration of the gas evolving unit 100 on an axis O. FIG. 4 is a cross-sectional view showing the configuration of the gas evolving unit 100 on the axis O.

The evolved gas analyzer 200 includes a body unit 202 that is a housing; an attaching unit 204 for a gas evolving unit, the attaching unit having a box shape and attached at a front surface of the body unit 202; and a computer (control device) 210 controlling the evolved gas analyzer. The computer 210 includes a CPU processing data, a memory unit storing a computer program and data, an input unit such as a monitor, a keyboard, etc.

In the attaching unit 204 for the gas evolving unit, there are a heating furnace (heating unit) 10 having a cylinder shape; a sample holder 20; a cooling unit 30; a splitter 40 splitting gas; and the gas evolving unit 100 having an ion source 50 as assembly. In addition, a mass spectrometer (detecting means) 110 is provided in the body unit 202. The mass spectrometer analyses gas components evolved by heating a sample.

In addition, an opening 204h is provided at an upper surface of the attaching unit 204 for the gas evolving unit, while being provided at a front surface thereof. The sample holder 20 is located at the opening 204h by being moved toward a discharging position that is located at an outside of the heating furnace 10. Therefore, a sample may be supplied on or removed from the sample holder 20 through the opening 204h. In addition, a slit 204s is provided at the front surface of the attaching unit 204. By moving an opening/closing handle 22H exposed to an outside of the attaching unit through the slit, the sample holder 20 is moved into or from the heating furnace 10. Therefore, the sample holder is set at the discharging position, and thus, the sample is supplied on or removed from the sample holder.

Figure 10:
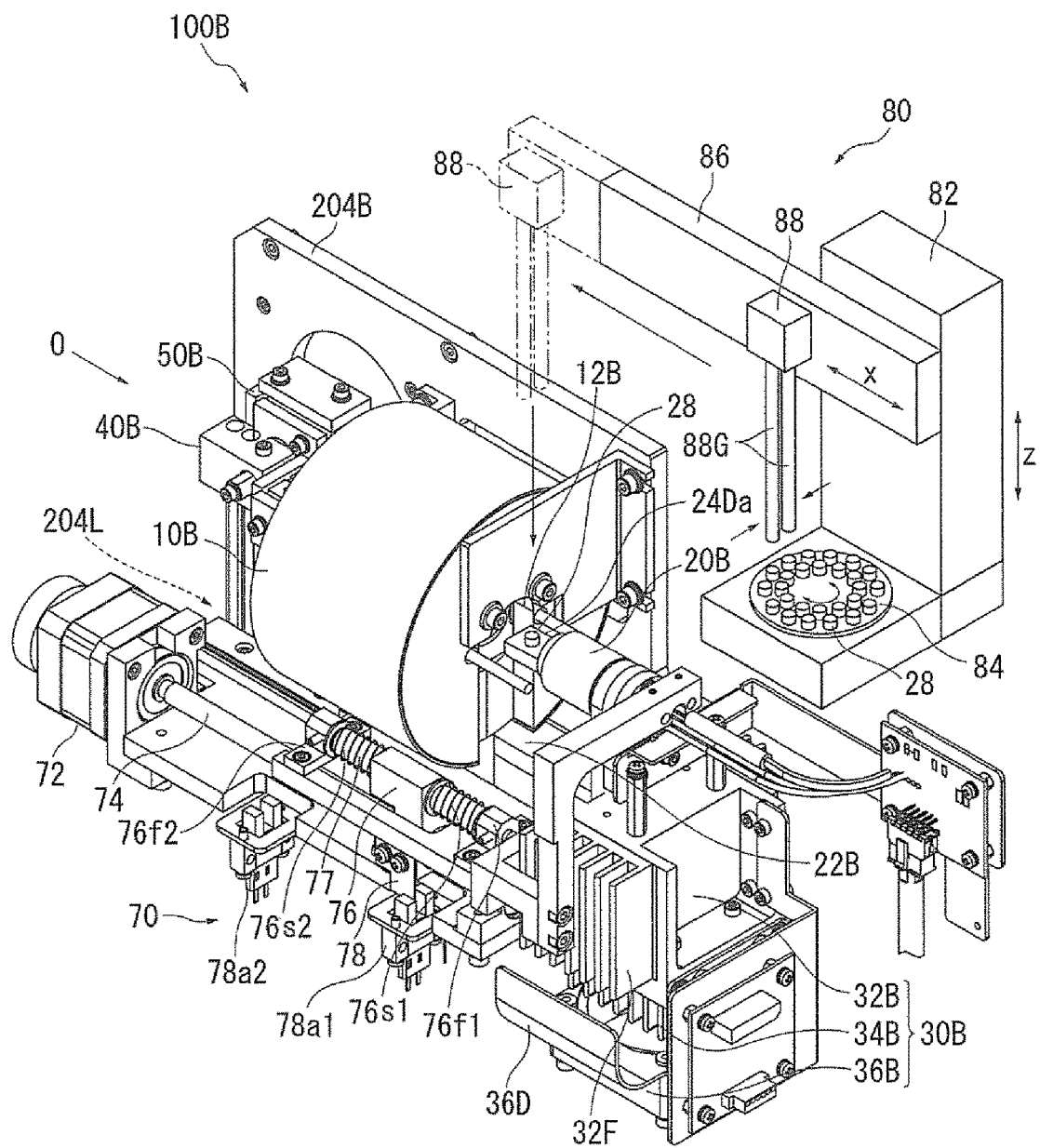
FIG. 10 is a perspective view showing the configuration of a gas evolving unit according to another exemplary embodiment of the present invention.

In addition, as shown in FIG. 10, when the sample holder 20 is moved on a movement rail 204L (after mentioned) by a stepping motor, etc. controlled by the computer 210 to control the sample holder 20, the sample holder 20 may be automatically moved into or from the heating furnace 10.

Hereinafter, the configuration of the gas evolving unit 100 will be described with reference to FIGS. 2 to 5.

First, the heating furnace 10 is attached to an attaching plate 204a of the attaching unit 204 by being parallel to the axis O. The heating furnace includes a heating chamber 12 having a cylinder shape and being opened on the axis O; a heating block 14; and a heat retaining jacket 16.

The heating block 14 surrounds the heating chamber 12, and the heat retaining jacket 16 surrounds the heating block 14. The heating block 14 is made of aluminum, and is heated by electricity from a pair of heating unit heaters 14a extending from the heating furnace 10 to outside in a direction of the axis O as shown in FIG. 4. The heating unit heaters 14a heat (retains the heat of) the heating block 14, and air in the heating chamber 12 surrounded by the heating block 14 to a predetermined temperature.

In addition, the attaching plate 204a extends in a direction perpendicular to the axis O. The splitter 40 and the ion source 50 are attached to the heating furnace 10. In addition, a supporter 204b extends in a vertical direction of the attaching unit 204, and supports a staying unit 55 of the ion source 50.

The splitter 40 is connected to an opposite side (right side of FIG. 3) of an opening side of the heating furnace 10. In addition, a carrier gas protecting pipe 18 is connected to a lower side of the heating furnace 10. The carrier gas protecting pipe 18 surrounds a carrier gas channel 18f connected to a lower surface of the heating chamber 12. Carrier gas C is introduced into the heating chamber 12 through the carrier gas channel.

In addition, a gas channel 41 communicates with a cross section on the opposite side (right side of FIG. 3) of an opening side of the heating chamber 12. Mixed gas M of both the carrier gas C and a gas component G evolved by the heating furnace 10 (heating chamber 12) flows through the gas channel 41.

The sample holder 20 includes a stage 22 moving on the movement rail 204L attached to an inner upper surface of the attaching unit 204; a bracket 24c attached on the stage 22 and extending in a vertical direction; insulators 24b and 26 attached to a front surface (left side of FIG. 3) of the bracket 24c; a sample holding unit 24a extending from the bracket 24c in a direction of the axis O in the heating chamber 12; a sample heater 27 provided just below the sample holding unit 24a; and a sample plate 28, on which the sample is placed, provided on an upper surface of the sample holding unit 24a above the sample heater 27.

Here, the movement rail 204L extends in a direction of the axis O (horizontal direction of FIG. 3), and the stage 22 of the sample holder 20 moves in the direction of the axis O. In addition, the opening/closing handle 22H extends in a direction perpendicular to the axis O, and is attached to the stage 22.

The movement rail 204L is a sample holder supporting unit in the appended claims.

In addition, an upper portion of the bracket 24c has a semicircular shape and a lower portion of the bracket has a rectangular shape. Referring to FIG. 6, the insulator 24b has a substantially cylinder shape, and is provided at a front surface of an upper portion of the bracket 24c. An electrode 27a of the sample heater 27 penetrates the insulator 24b, and protrudes to an outside of the gas evolving unit. The insulator 26 has a rectangular shape, and is provided at the front surface of the bracket 24c. The insulator 26 is located lower than the insulator 24b. In addition, the insulator 26 is not provided at a lower portion of the bracket 24c, and a front surface of the lower portion of the bracket 24c is exposed to form a contact surface 24f.

The bracket 24c has a diameter slightly larger than a diameter of the heating chamber 12 such that the bracket 24c seals the heating chamber 12. The sample holding unit 24a is located in the heating chamber 12.

In addition, the sample placed on the sample plate 28 in the heating chamber 12 is heated in the heating furnace 10 such that the gas component G is evolved.

The cooling unit 30 faces the bracket 24c of the sample holder 20, and is located outside of the heating furnace 10 (left side of the heating furnace 10 in FIG. 3). The cooling unit 30 includes a cooling block 32 having a concave portion 32r that has a rectangular shape; air cooling fins 34 connected to a lower surface of the cooling block 32; and a air cooling fan 36 connected to a lower surface of the pneumatic cooling fins 34, and blowing air to the air cooling fins 34.

In addition as explained in detail after, when the sample holder 20 moves in a direction of the axis O on the movement rail 204L toward a left side of FIG. 3, and comes out of the heating furnace 10, the contact surface 24f of the bracket 24c is positioned at the concave portion 32r of the cooling block 32 by being in contact with the concave portion. Consequently, as heat of the bracket 24c is removed by the cooling block 32, the sample holder 20 (particularly, the sample holding unit 24a) is cooled.

In addition, according to the exemplary embodiment of the present invention, the sample holder 20 (including the bracket 24c) and the cooling block 32 are made of aluminum.

As shown in FIGS. 3 and 4, the splitter 40 includes the gas channel 41 connected to the heating chamber 12; a branching channel 42 connected to the gas channel 41, and opened to the outside; a mass flow controller (discharged flow rate controlling device) 42a connected to a discharge side of the branching channel 42 to control flow rate of the mixed gas M discharged from the branching channel 42 to the outside; a housing unit 43 opening the gas channel 41 therein; and a heat retaining unit 44 surrounding the housing unit 43.

As shown in FIG. 4, when viewed from the top, the gas channel 41 is connected to the heating chamber 12 and extends in a direction of the axis O and next, bends in a direction perpendicular to the axis O, and bends again in a direction of the axis O such that the gas channel reaches an end part 41e. The gas channel has a crank shape. In addition, a portion of the gas channel 41 that extends in a direction perpendicular to the axis O is provided with a center thereof having a circular shape that has a diameter larger that a diameter of the gas channel to define a branch chamber 41M. The branch chamber 41M extends to an upper surface of the housing unit 43. The branch chamber 41M is fitted with the branching channel 42 having a diameter slightly smaller than that of the branch chamber 41M.

The gas channel 41 may have a straight line shape extending in a direction of axis O from the heating chamber 12 connected with the gas channel to the end part 41e. Alternatively, depending on a positional relationship with the heating chamber 12 or with the ion source 50, the gas channel 41 may have various curved shapes, a line shape having an angle to the axis O, etc.

In addition, according to the exemplary embodiment of the present invention, the gas channel 41 has a diameter about 2 mm, and the branch chamber 41M and the branching channel 42 have respective diameters about 1.5 mm. In addition, a ratio (split ratio) of flow rates from the gas channel 41 to the end part 41e, and flow rates branched to the branching channel 42 is determined by flow resistance.

The mixed gas M may flow more through the branching channel 42. In addition, the split ratio is controlled by adjusting an opening ratio of the mass flow controller 42a.

As shown in FIGS. 3 and 4, the ion source 50 includes an ionizer housing unit 53; an ion heat retaining unit 54 surrounding the ionizer housing unit 53; a discharge needle 56; and a staying unit 55 fixing the discharge needle 56. The ionizer housing unit 53 has a plate shape, and a surface of the plate is parallel to the axis O. A small hole 53C penetrates the center of the surface of the plate. In addition, the end part 41e of the gas channel 41 passes through the ion ionizer housing unit 53, and faces a side wall of the small hole 53C. In the meantime, the discharge needle 56 extends in a direction perpendicular to the axis O, and faces the small hole 53C.

In addition, in the mixed gas M introduced around the small hole 53C from the end part 41e, the gas component G is ionized by the discharge needle 56.

The ion source 50 is a well-known device. According to the exemplary embodiment of the present invention, atmospheric pressure chemical ionization (APCI) is applied to the ion source. APCI causes minimal fragmentation of the gas component G, such that fragmentation peak does not occur. Therefore, it is possible to detect the measurement target without separating the gas component G by using a chromatograph, etc.

The gas component G ionized at the ion source 50 and the carrier gas C are introduced to the mass spectrometer 110, and are analyzed.

In addition, the ion source 50 is contained in the ion heat retaining unit 54.

As shown in FIG. 4, an inner surface of the heating chamber 12 (an inner wall of the heating block 14) is enlarged toward an outside at a position around the sample plate 28 in the sample holder, thereby forming a recess 14r. Therefore, it is possible to prevent flow of the gas component G from being stagnant due to a narrow space between the sample and the inner surface of the heating chamber 12.

Figure 9:
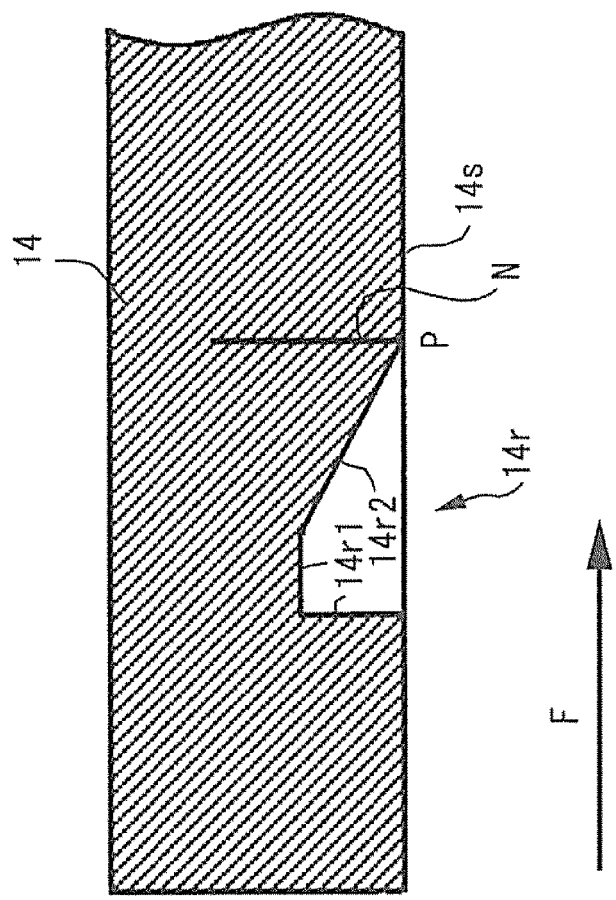
FIG. 9 is a partial longitudinal sectional view showing a recess positioned at an inner surface of the heating chamber.

FIG. 9 is a partial longitudinal sectional view showing the recess 14r positioned at a part of an upper portion of the heating block 14 of FIG. 3. As shown in FIG. 9, the recess 14r has a first recess portion 14r1 and a second recess portion 14r2 integrally. The first recess portion is located upstream in a flow direction F of the gas component G, and the second recess portion is located downstream of the first recess portion 14r1 in the flow direction F, and meets the inner surface of the heating chamber 12 (the inner wall 14s of the heating block 14). In addition, the first recess portion 14r1 is vertically depressed from the inner wall 14s, and has a bottom surface parallel to the inner wall 14s, and is connected to the second recess portion 14r2.

Here, when viewed from a cross section of FIG. 9 (namely, the cross section along the flow direction F), an outline (line) of the second recess portion 14r2 is located upstream of a normal of the inner wall 14s relative to a contact point P between the second recess portion 14r2 and the inner wall 14s in the flow direction F. Therefore, since the outline (line) of the second recess portion 14r2 is oblique downstream in the flow direction F, the gas component G easily flows along the second recess portion 14r2 downstream in the flow direction F (namely, toward the detecting means (mass spectrometer) 110). In addition, the outline (line) of the second recess portion 14r2 may be a straight line shown in FIG. 9 or a curved line.

In addition, the flow direction F is a direction from the contact point P to the detecting means (mass spectrometer) 110.

Figure 5:
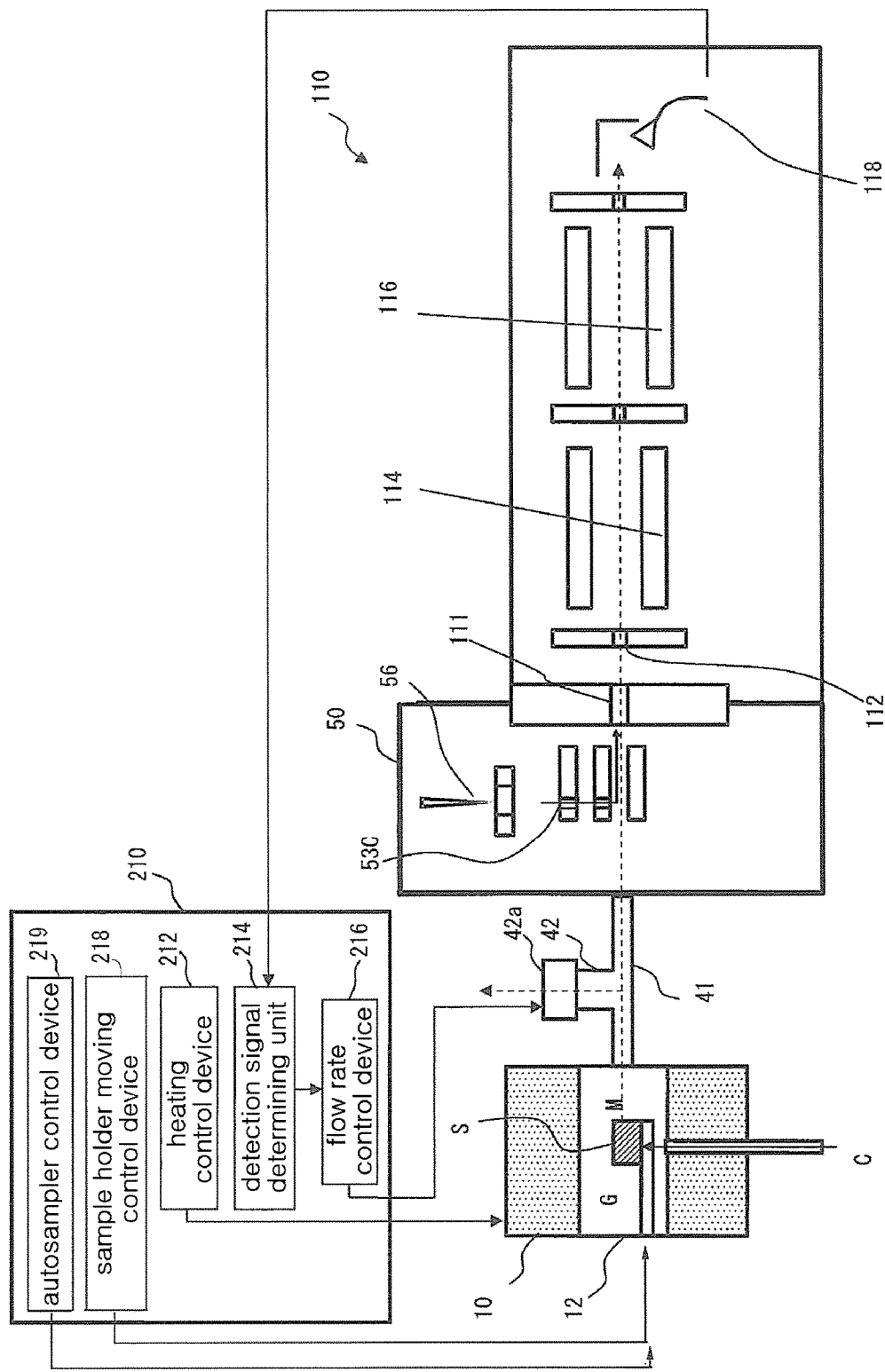
FIG. 5 is a block diagram showing a process of analyzing a gas component by the evolved gas analyzer.

FIG. 5 is a block diagram showing a process of analyzing a gas component by the evolved gas analyzer 200.

The sample S is heated in the heating chamber 12 of the heating furnace 10, and the gas component G is evolved. Heating condition (temperature rising rate, maximum temperature, etc.) of the heating furnace 10 is controlled by a heating control device 212 of the computer 210.

The gas component G is mixed with the carrier gas C introduced in the heating chamber 12 to be a mixed gas M, and the mixed gas M is introduced in the splitter 40. A detection signal determining unit 214 of the computer 210 receives a detection signal from a detector 118 of the mass spectrometer 110.

A flow rate control device 216 determines whether or not peak intensity of the detection signal received from the detection signal determining unit 214 is within a threshold range. When the peak intensity is out of the threshold range, the flow rate control device 216 controls the opening ratio of the mass flow controller 42a. Therefore, flow rate of the mixed gas M discharged from the splitter 40 to an outside through the branching channel 42 is controlled, and further, flow rate of the mixed gas M introduced from the gas channel 41 into the ion source 50 is controlled, thereby optimizing a detection accuracy of the mass spectrometer 110.

The mass spectrometer 110 includes a first fine hole 111 through which the gas component G ionized at the ion source 50 is introduced; a second fine hole 112 through which the gas component G flows, after the first fine hole 111; an ion guide 114; a quadrupole mass filter 116; and the detector 118 detecting the gas component G discharged from the quadrupole mass filter 116.

The quadrupole mass filter 116 varies an applied high frequency voltage such that mass is scanned. The quadrupole mass filter generates a quadrupole electric field, and detects ions by moving the ions like a pendulum swinging within the quadrupole electric field. The quadrupole mass filter 116 functions as a mass separator passing only gas component G within a certain mass range such that the detector 118 may identify and quantify the gas component G.

In addition, in comparison with an entire ions detection (scan) mode detecting ions of a certain range of a mass-to-charge ratio, when using a selected ion detection (SIM) mode detecting only ions of a certain mass-to-charge ratio m/z of a gas component, which is a measurement target, a detection accuracy of the gas component, which is the measurement target, increases.

Hereinafter, cooling of the sample holder 20 will be described with reference to FIGS. 6A and 6B. According to the exemplary embodiment of the present invention, the sample holder 20 moves in the direction of axis O intervened by the stage 22 between predetermined two positions (a discharging position at which the sample plate 28 is discharged and located at an outside of the heating furnace 10 as shown in FIG. 6A, and a measuring position at which the gas component is measured and the sample plate 28 is located in the heating furnace 10 as shown in FIG. 6B).

Figure 6A:
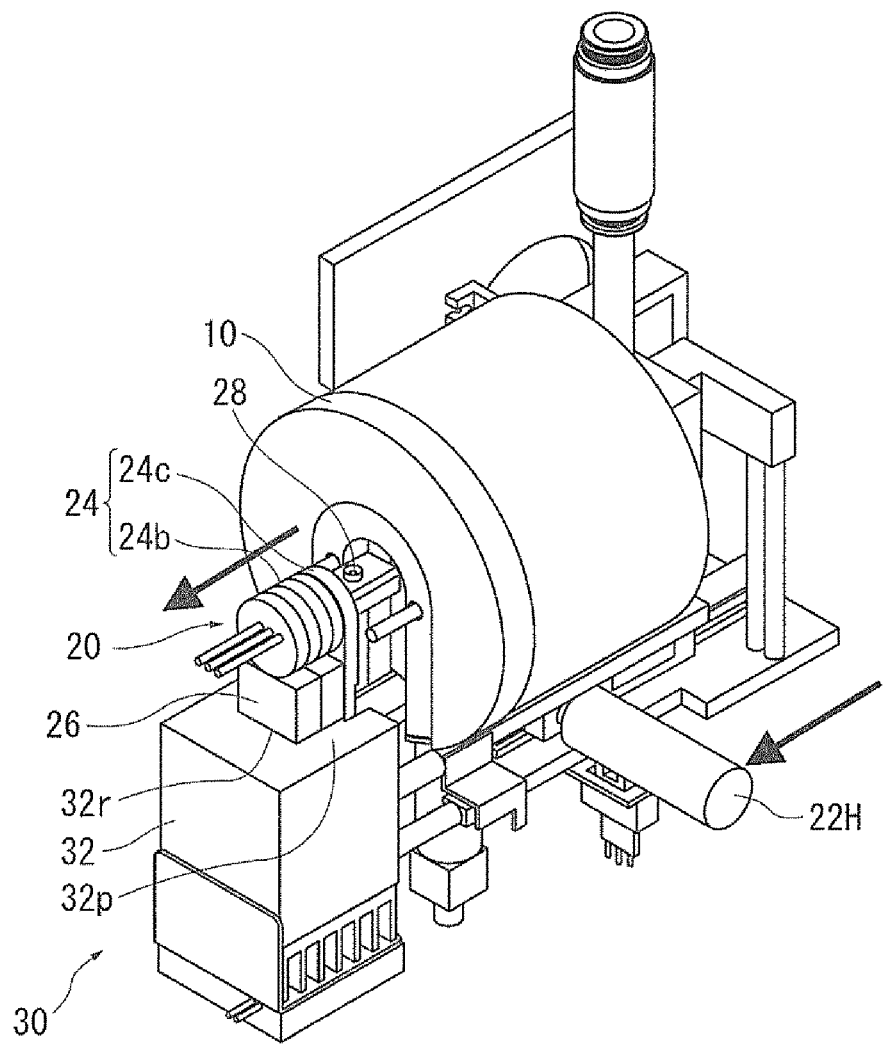
FIGS. 6A and 6B are views respectively showing a discharging position and a measuring position of the sample holder.
Figure 6B:
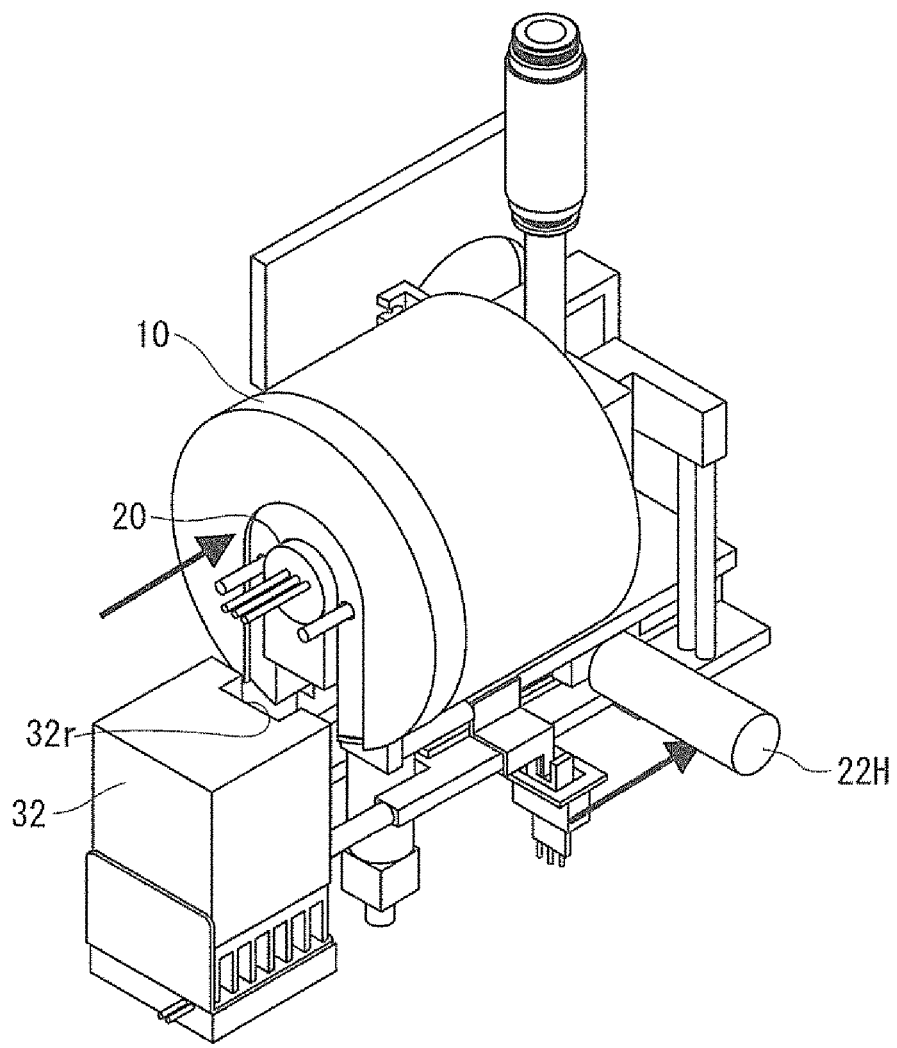

First, at the discharging position shown in FIG. 6A, when the sample plate 28 and the sample are supplied on or removed from the sample holder, the sample plate 28 and the sample are replaced, and are heated from about a room temperature to start the next analysis. Here, in case when the sample holder 20 is too hot, when the sample plate 28 is located in the sample holder, the sample begins to be heated in advance of the analysis. Therefore, in order to prevent this, the sample holder 20 is naturally cooled, but standby time to cool the sample holder 20 is too long.

Therefore, as shown in FIG. 6A, when the sample holder 20 is moved to the discharging position, the contact surface 24f of the bracket 24c is in contact with the concave portion (contact portion) 32r of the cooling block 32. Therefore, heat of the bracket 24c is cooled by the cooling block 32, and thus the sample holder 20 is cooled.

In comparison with the natural cooling, the sample holder 20 is rapidly cooled, and thus it is possible to enhance the analysis work efficiency. In addition, the sample holder 20 is cooled at an outside of the heating furnace 10 such that the cooling unit 30 is not exposed to high temperature air of the heating furnace 10. Therefore, excessive cooling performance is unnecessary, and the cooling unit 30 or the entire apparatus is provided in a small size. In addition, the temperature of the heating block 14 is not reduced by the cooling, such that it is unnecessary to use extra energy and time to heat the heating furnace 10 again.

In addition, it is unnecessary to provide the cooling unit 30 in the heating furnace 10, whereby the heating furnace 10 or the entire apparatus may be provided in a small size.

Figure 7:
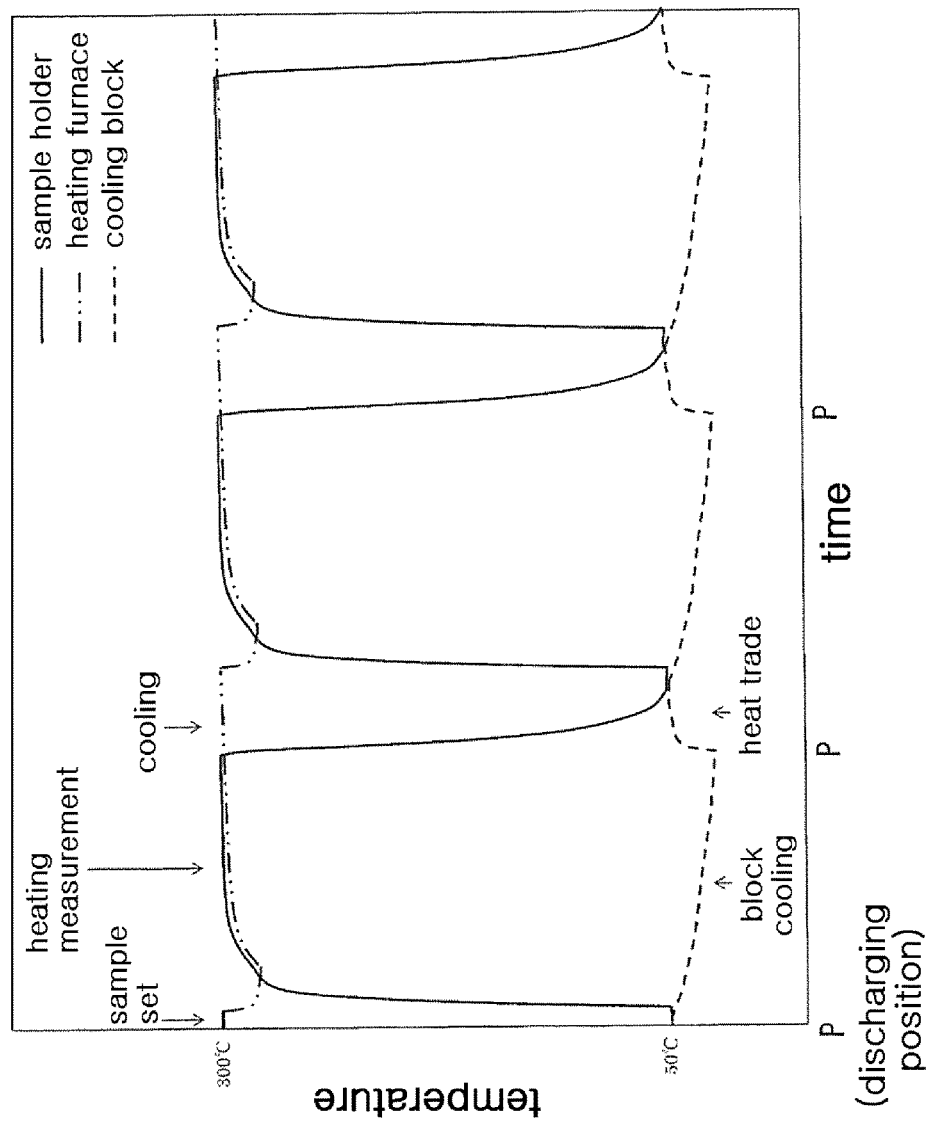
FIG. 7 is a view showing an example of a heating pattern of a heating unit, and of temperature changes of both a sample holder and a cooling unit.

FIG. 7 is a view showing an example of a heating pattern of the heating furnace 10 controlled by the heating control device 212, and of temperature changes of both the sample holder 20 and the cooling block 32. Here, retention temperature (maximum temperature) of the heating furnace 10 is 300° C., and heating start temperature of the sample is under 50° C.

First, at time 0 (when the sample holder 20 is moved to the discharging position P of FIG. 6A), the sample is placed on the sample plate 28 of the sample holder 20 having 50° C. Here, the cooling block 32 has been already cooled to a room temperature, and the cooling block is heated up to about 50° C. by being in contact with the sample holder 20. In the meantime, the sample holder 20 is heated to about 50° C. In addition, air temperature in the heating furnace 10 is controlled by the heating unit heater 14a to be 300° C.

Next, the sample holder 20 cooled to about 50° C. is moved to the measuring position of FIG. 6B. When the sample holder is moved into the heating chamber 12, the heating furnace 10 controlled to be 300° C. and the sample heater 27 provided in just below the sample holding unit 24a cause the sample holder 20 to be heated to 300° C., and an evolved gas component is analyzed. During the analyzing, the cooling block 32 is cooled to under 50° C. (about room temperature) by the air cooling fan 36, etc.

After the analysis, the sample holder 20 is moved to the discharging position P again, and the above-described heating cycle is repeated.

Here, the cooling unit 30 is provided at an outside of the heating furnace 10, and the cooling unit 30 heated by cooling the sample holder 20 is slowly cooled during the analysis. Particularly, as shown in FIG. 7, generally, time for the analysis is longer than time for cooling. Therefore, it is unnecessary to rapidly cool the cooling unit 30 by using water cooling, etc. It is sufficient to apply natural cooling by the air cooling fins 34, or apply forced air cooling by the air cooling fan 36. In comparison with the water cooling, etc., the structure of the cooling unit 30 is simple, whereby the entire apparatus may have reduced costs or may be provided in a small size.

In addition, as shown in FIG. 6A, when viewed from the top of the cooling block 32, a pair of protruding portions 32p having a U shape protrudes from respective opposite ends of the concave portion (contact portion) 32r toward the heating furnace 10 so as to surround the sample holder 20 by the protruding portions 32p. Therefore, the sample holder 20 is moved to the concave portion 32r to be sufficiently located at an outside of the heating furnace 10. In addition, capacity (heat capacity) of the cooling block 32 increases by comparison with a cooling block having no protruding portions 32p, thereby enhancing cooling performance.

In addition, in order to maintain the same capacity of the cooling block 32 without the protruding portions 32p, it is required to move the cooling block 32 more toward an outside (left side of FIG. 6A) of the heating unit 10, whereby it results in a large size of the entire apparatus. Therefore, it is possible to provide the entire apparatus in a small size by providing the protruding portions 32p.

In addition, when a ratio C1/C2 of a heat capacity C1 of the cooling block 32 to a heat capacity C2 of the sample holder 20 is within a range of 5 to 20, it is possible to provide the entire apparatus in a small size and to enhance cooling performance. When the ratio is less than 5, the heat capacity C1 of the cooling block 32 is reduced, and thus the cooling performance may also be reduced. If the cooling performance is insufficient, the cooling block may not be sufficiently cooled to the heating start temperature. When the ratio exceeds 20, the size of the cooling block 32 is too large, whereby it results in a large size of the entire apparatus.

In addition, it is desired that the cooling unit 30 is provided with the air cooling fan 36 or with the air cooling fins 34 cooling the cooling block 32. Therefore, the structure of the cooling unit 30 is simple, and thus, the entire apparatus may have reduced costs or may be provided in a small size, in comparison with the case when water cooling is applied to the cooling unit 30 or with the case when a duct, which refrigerant gas flows through, is attached to the cooling unit 30.

In case of a heat sink provided with the air cooling fins 34 attached to the cooling block 32, the air cooling fins 34 naturally cool the cooling block 32.

However, when the cooling block 32 is insufficiently cooled, it is desired that the air cooling fan 36 is also attached thereto so as to apply forced air cooling to the cooling block 32. In addition, according to the exemplary embodiment of the present invention, as shown in FIGS. 2, 6A and 6B, the air cooling fins 34 are connected to the lower surface of the cooling block 32, and the air cooling fan 36 is connected to the lower surface of the air cooling fins 34.

In addition, according to the exemplary embodiment of the present invention, the heating furnace 10 includes both the heating unit heater 14a heating an inside of the heating furnace (heating chamber 12) to a predetermined temperature, and the sample heater 27 heating the sample in the sample holder 20.

Therefore, the heating unit heater 14a heats (retains the heat of) air in the heating furnace (heating chamber 12) to the predetermined temperature such that it is possible to prevent the temperature of the sample in the heating chamber 12 from being changed. In addition, the sample heater 27 provided around the sample may locally heat the sample, and thus, the temperature of the sample rapidly increases.

In addition, in terms of rapidly increasing the temperature of the sample, it is desired that the sample heater 27 is positioned around a unit on which the sample is placed (for example, the sample plate 28). Particularly, it is desired that the sample heater 27 is provided under the sample plate 28 in the sample holder 20.

Hereinafter, a method for analyzing evolved gas according to the exemplary embodiment of the present invention will be described with reference to FIG. 8.

First, by using the evolved gas analyzer 200 shown in FIGS. 1 to 5, the sample plate 28 on which the sample is placed is positioned (on the sample holding unit 24a) in the sample holder 20 at the discharging position at step S2.

Next, the sample holder 20 is moved into the heating furnace 10 by being moved to the measuring position at step S4. In addition, the sample heater 27 heats the sample holder 20 to a predetermined temperature at step S6. In addition, the sample holder 20 is heated by the heating furnace 10, and specifically, is precisely heated by the sample heater 27 provided under the sample holding unit 24a to the predetermined temperature.

The ion source 50 ionizes a gas component evolved by heating the sample, and a mass spectrometer 110 analyzes the ionized gas component at step S8.

After the analysis, the sample heater 27 stops heating at step S10, and the sample holder 20 is discharged from the heating furnace 10 by being moved to the discharging position at step S12.

While the sample holder 20 (contact surface 24f) is in contact with the cooling block 32 at the discharging position, the sample holder 20 is cooled to a predetermined temperature at step S14.

After the cooling, the sample placed on the sample plate 28 is removed from the sample holder 20 at step S16.

After the analysis, when determination is 'Yes' at step S18, the processing is terminated. When determination is 'No' at step S18, the process goes back to step S2 so as to analyze another sample.

Figure 8:
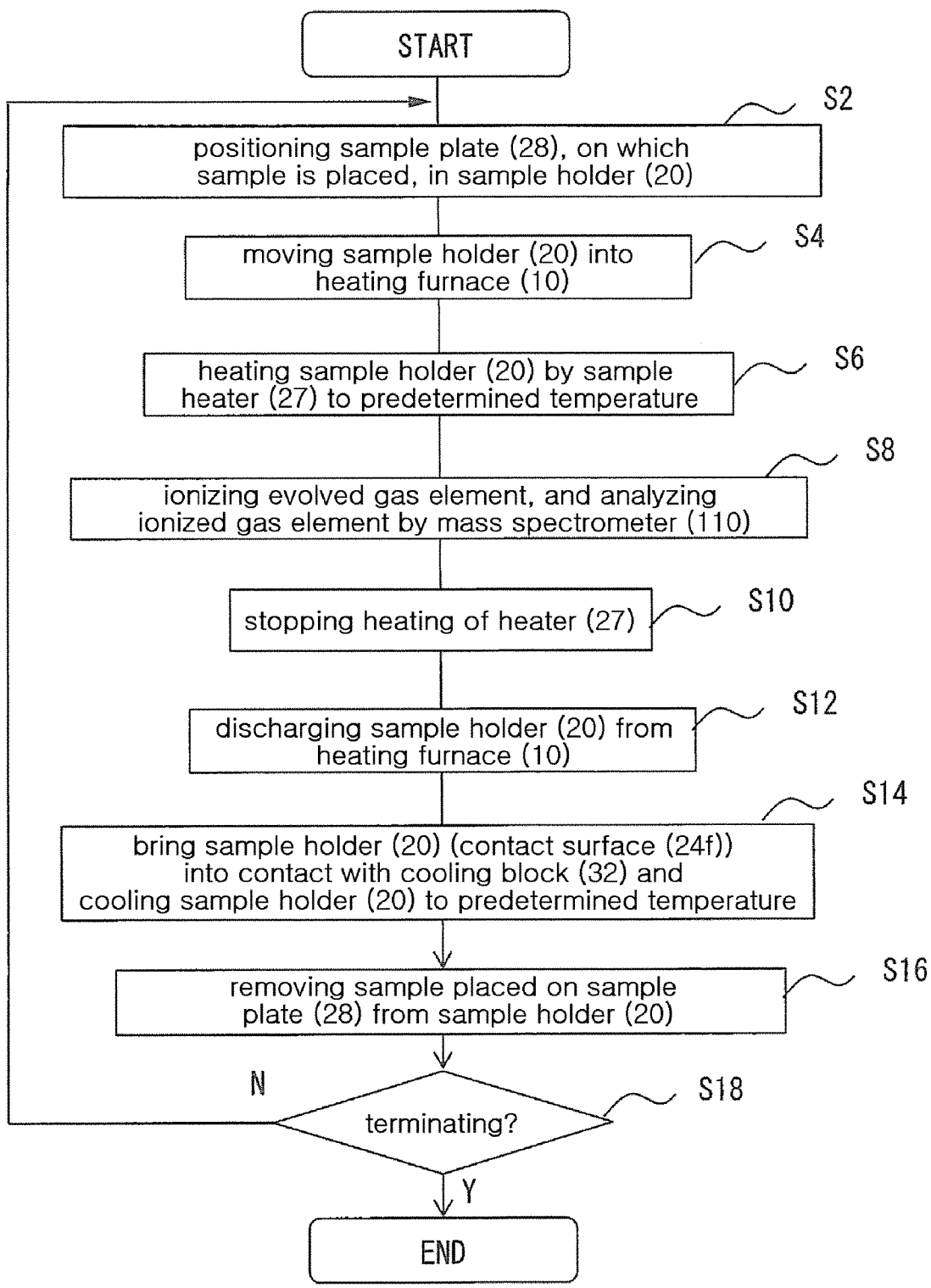
FIG. 8 is a flowchart showing a method for analyzing evolved gas according to the exemplary embodiment of the present invention.

The processes shown in FIG. 8 may be automatically performed by the computer 210 by applying the configuration of a gas evolving unit of FIG. 10.

FIG. 10 is a perspective view showing the configuration of a gas evolving unit 100B according to another exemplary embodiment of the present invention. The gas evolving unit 100B includes a heating furnace 10B; a sample holder 20B; a cooling unit 30B; a splitter 40B; an ion source 50B; a sample holder moving unit 70; and an autosampler 80. The heating furnace 10B, the sample holder 20B, the splitter 40B, and the ion source 50B are the same as those of the gas evolving unit 100 of FIG. 2, and thus, a detailed description thereof will be omitted. In addition, the gas evolving unit 100B is attached to an attaching unit 204B for the gas evolving unit of an evolved gas analyzer (not shown).

The sample holder 20B is attached to a stage 22B moving on a movement rail 204L attached to an inner upper surface of an attaching unit 204B. The movement rail 204L extends in a direction (horizontal direction of FIG. 10) of an axis O of the heating furnace 10B, and the stage 22B of the sample holder 20B moves in the direction of the axis O.

The sample holder moving unit 70 is operated in the direction of the axis O by using a ball thread, and includes a stepping motor 72; a screw shaft 74 connected to the stepping motor 72; a nut unit 76 being coupled to the screw shaft 74 by screw-type engagement; and a sensor plate 78 attached to the nut unit 76.

In addition, the stage 22B is connected to the nut unit 76, and the nut unit 76 is operated in the direction of the axis O by rotation of the screw shaft 74, and thus, the stage 22B and the sample holder 20B also move in the direction of the axis O.

Specifically, a sample holder moving control device 218 (referring to FIG. 5) of a computer 210 controls rotation of the stepping motor 72 to move the sample holder 20B, whereby steps S6 to S14 may be automatically performed.

Here, the sensor plate 78 is attached to the nut unit 76. In the meantime, a first sensor 78a1 and a second sensor 78a2, which are photoelectric sensors, are respectively close to the discharging position and the measuring position (referring to FIGS. 6A and 6B) of the sample holder 20B. Therefore, when the sample holder 20B is close to the discharging position or to the measuring position, the sensor plate 78 blocks a photoelectric receiver of the first sensor 78a1 or a photoelectric receiver of the second sensor 78a2. Accordingly, a position of the nut unit 76, and moreover, a position of the sample holder 20B may be detected by the sample holder moving control device 218.

In addition, the nut unit 76 is supported by a shaft 77 parallel to the axis O, and moves along the shaft 77. Nut unit brackets 76f1 and 76f2 are respectively attached to opposite ends of the shaft 77. The first spring part 76s1 surrounds an outer circumference of the shaft 77 positioned between the nut unit bracket 76f1 and the nut unit 76, and the second spring part 76s2 surrounds outer circumference of the shaft 77 positioned between nut unit bracket 76f2 and the nut unit 76.

Therefore, when the sample holder 20B is close to the discharging position, the first spring part 76s1 is compressed, and the first spring part elastically biases the sample holder 20B in a direction towards the cooling unit 30B (right side of FIG. 10) by using repulsive power. In case when the first spring part 76s1 is not used, it is difficult to distinguish a last position of the sample holder due to not resistance in the direction of the axis O, when the sample holder 20B is close to the discharging position and the sample holder 20B is in contact with the cooling unit 30B. Therefore, it may be difficult to precisely bring the sample holder 20B into contact with the cooling unit 30B.

Therefore, when the sample holder 20B is close to the discharging position, the first spring part 76s1 applies resistance in the direction of the axis O. Against the resistance, rotation of the stepping motor 72 is controlled to push the nut unit 76, and moreover, the sample holder 20B toward the cooling unit 30B, whereby the sample holder 20B is precisely in contact with the cooling unit 30B.

In the same manner as the first spring part, the second spring part 76s2 is compressed when the sample holder 20B is close to the measuring position. The second spring part elastically biases the sample holder 20B in a direction towards the heating furnace 10B (left side of FIG. 10) by using repulsive power. Therefore, when the sample holder 20B is close to the measuring position, the second spring part 76s2 applies resistance in the direction of the axis O. Against the resistance, rotation of the stepping motor 72 is controlled to push the nut unit 76, and moreover, the sample holder 20B toward the heating furnace 10B, whereby the sample holder 20B is precisely located at the measuring position.

In addition, by the autosampler 80 of FIG. 11, the sample may be automatically supplied on or removed from the sample holder 20B at an outside, whereby steps S2 to S18 may be automatically performed.

The autosampler 80 includes a base 82; a sample rack 84 having a disc shape provided on the base 82; an arm 86 attached to the base 82, and moving in a vertical direction (Z axis) and in a horizontal direction (X axis) relative to the base 82; a gripper base unit 88 attached to the arm; and a pair of grippers 88G (gripping unit) extending from the gripper base unit 88 downwardly.

A plurality of sample plates 28 are placed on the sample rack 84, and the sample rack 84 rotates little by little to move the sample plate 28 to a position at which the sample plate is picked up by the grippers 88G. In addition, the grippers 88G grip the sample plate 28 therebetween, and moves with the arm 86.

Specifically, an autosampler control device 219 (referring to FIG. 5) of the computer 210 controls the arm 86 and the grippers 88G, and the sample plate 28, which was analyzed, is removed from the sample holder 20B at the discharging position. Next sample plate 28, which will be analyzed, is placed on the sample holder 20B from the sample rack 84 by the grippers 88G, whereby analysis may be continuously automatically operated.

In addition, referring to FIG. 10, air cooling fins 34B are connected to a lower surface of the cooling block 32B, and air cooling fins 32F are connected to each of opposite side surfaces of the cooling block 32B (side surfaces perpendicular to a direction of the axis O). In addition, the air cooling fan 36B is provided at a lower surface of the air cooling fins 34B connected to a lower surface of the cooling block 32B.

In the meantime, a fan duct 36D extends from the air cooling fan 36B toward an outside of the air cooling fins 32F connected to a side surface of the cooling block 32B.

Therefore, the cooling block 32B is cooled by the air cooling fins 32F and 34B connected to the lower surface and the side surface of the cooling block. In addition, the fan duct 36D functions as an air guiding plate guiding cooling air from the air cooling fan 36B to the air cooling fins 32F, whereby the cooling block 32B is efficiently cooled.

In addition, in order to seal a part through which the gas component G, the carrier gas C or the mixed gas M flows in the evolved gas analyzer, it is desirable to seal a junction of the part with a carbon sheet. The part may be a junction of the carrier gas protecting pipe 18 and the carrier gas channel 18f.

It should be understood that the exemplary embodiment according to the concept of the present invention is not limited to the exemplary embodiment, but various modifications, equivalents, additions and substitutions are possible, without departing from the scope and spirit of the invention.

Besides phtalates, the measurement target may be brominated flame retardants (polybrominated biphenyl (PBB), polybrominated diphenyl ether (PBDE)) restricted under RoHS, without being limited thereto.

The sample holder supporting unit movably supporting the sample holder may be an arm, etc. besides the above described rail.

Components, shapes, configurations, etc. of the heating furnace, the sample holder, and the cooling unit are not limited to the exemplary embodiments. In addition, the detecting means is not limited to the mass spectrometer.

In addition, without being limited to the case that the sample holder is in direct contact with the cooling unit, a unit may be provided to be in contact with the sample holder, and the unit may be in direct contact with the cooling unit (that is, the sample holder is in indirect contact with the cooling unit).

What is claimed is:

1. An evolved gas analyzer, comprising:
   a sample holder, holding a sample;
   a heating furnace, receiving the sample holder therein, and evolving a gas component by heating the sample;
   a detecting means detecting the gas component evolved by the heating furnace;
   a sample holder supporting unit supporting the sample holder so as to enable moving the sample holder to given positions inside and outside of the heating furnace; and a cooling unit placed outside of the heating furnace, cooling the sample holder by direct or indirect contact with the sample holder, when the sample holder is moved to a discharging position at which the sample can be put in or taken out, wherein the cooling unit comprises a cooling block in contact with the sample holder, an air cooling fan, air cooling fins and a fan duct, cooling the cooling block, the air cooling fins are connected to a floor portion and a side surface of the cooling block, the air cooling fan is placed at a lower part of the air cooling fin connected to the floor portion of the cooling block, and the fan duct extends from the air cooling fan towards outside of the air cooling fin connected to the side surface of the cooling block, and forms an air guiding plate guiding cooling air from the air cooling fan to the air cooling fins.

2. The apparatus of claim 1, wherein the cooling block comprises:

a contact portion being in contact with the sample holder at the discharging position; and a protruding portion extending more towards the heating furnace to form a recess in the cooling block to surround the sample holder.

3. The apparatus of claim 1, wherein a ratio (C1/C2) of a heat capacity (C1) of the cooling block to a heat capacity (C2) of the sample holder is between 5 and 20.

4. The apparatus of claim 1, wherein the heating furnace comprises a heating furnace heater heating inside of the heating furnace to a given temperature, and the sample holder comprises a sample heater heating the sample.

5. The apparatus of claim 1, further comprising:

an autosampler automatically putting in or taking out the sample to or from the sample holder from outside; and a sample holder moving unit, moving the sample holder in conjunction with the autosampler, wherein the sample holder moving unit comprises:

a first spring part elastically pressuring the sample holder in a direction towards the cooling unit, when the sample holder is close to the discharging position; and a second spring part elastically pressuring the sample holder in a direction towards the heating furnace, when the sample holder is received inside the heating furnace and close to a measuring position at which measurement is performed.

6. The apparatus of claim 1, wherein a part of an inner wall of the heating furnace around the sample held in the sample holder expands towards outside, forming a recess, the recess comprising a first recess portion, which is located upstream of direction of flow of the gas component inside the heating furnace, and a second recess portion, which is located downstream compared to the first recess portion in the direction of flow direction and meeting the inner wall, as an integral body, and, when viewed from a cross section of the heating furnace along the direction of flow, an outline of the second recess portion is located more upstream of the direction of flow than a normal line of the inner wall at a contact point between the second recess portion and the inner wall.

7. A method for analyzing evolved gas, the method comprising:

supporting a sample holder holding a sample so as to enable moving the sample holder to given positions inside or outside of a heating furnace;

receiving the sample holder in the heating furnace to heat the sample;

detecting evolved gas components; and cooling the sample holder by bringing the sample holder into contact with a cooling block of a cooling unit, placed outside of the heating furnace, when the sample holder is moved to a discharging position at which the sample can be put in or taken out to or from the sample holder, wherein the cooling unit further comprises an air cooling fan, air cooling fins and a fan duct, cooling the cooling block, the air cooling fins are connected to a floor portion and a side surface of the cooling block, the air cooling fan is placed at a lower part of the air cooling fin connected to the floor portion of the cooling block, and the fan duct extends from the air cooling fan towards outside of the air cooling fin connected to the side surface of the cooling block, and forms an air guiding plate guiding cooling air from the air cooling fan to the air cooling fins.

\* \* \* \* \*